United States Patent [19]

Haendle et al.

[11] 4,149,082

[45] Apr. 10, 1979

[54] X-RAY DIAGNOSTIC INSTALLATION FOR X-RAY TOMOGRAPHIC IMAGES

[75] Inventors: Joerg Haendle; Hartmut Sklebitz, both of Erlangen, Fed. Rep. of Germany

[73] Assignee: Siemens Aktiengesellschaft, Berlin & Munich, Fed. Rep. of Germany

[21] Appl. No.: 866,017

[22] Filed: Dec. 30, 1977

[30] Foreign Application Priority Data

Mar. 21, 1977 [DE] Fed. Rep. of Germany ....... 2712320

[51] Int. Cl.$^2$ ............................................... A61B 6/02
[52] U.S. Cl. ................................................ 250/445 T
[58] Field of Search .................... 250/445 T, 314, 313, 250/460

[56] References Cited

U.S. PATENT DOCUMENTS

| 2,491,224 | 12/1949 | Stava | 250/445 T |
| 3,665,184 | 5/1972 | Schagen | 250/314 |

OTHER PUBLICATIONS

Klotz et al., "X-Ray 3-D Coded Aperture Imaging: Displaying the Heart," *Applied Optics*, Aug. 1976, vol. 15, No. 8, pp. 1913–1918.

*Primary Examiner*—Alfred E. Smith
*Assistant Examiner*—T. N. Grigsby
*Attorney, Agent, or Firm*—Hill, Gross, Simpson, Van Santen, Steadman, Chiara & Simpson

[57] ABSTRACT

In one mode, laminographic images are produced by sequentially pulsing a series of X-ray tubes, and by stepwise shifting of the image field of an image intensifier in an opposite sense so that each image of the desired layer is superimposed at the image intensifier output. The amplitude of the required magnetic deflection of the image intensifier is a function of the depth of the layer, and may be calibrated to represent the length dimension of a selected layer region. In another mode, a transverse sectional image is scanned by progressively increasing the magnetic deflection after each cycling of the X-ray sources, so as to scan at successive depths. With a video camera scanning the image intensifier output, one video line of each field may be stored for each depth, and then read out to display the cross sectional image. By storing different lines for respective different depths, oblique sections may be recorded. By sequentially pulsing right and left rows of X-ray sources in successive field intervals of the video camera, stereoscopic images may be generated, the right and left fields being suitably offset and visually differentiated (e.g. by color) for stereoscopic display.

10 Claims, 10 Drawing Figures

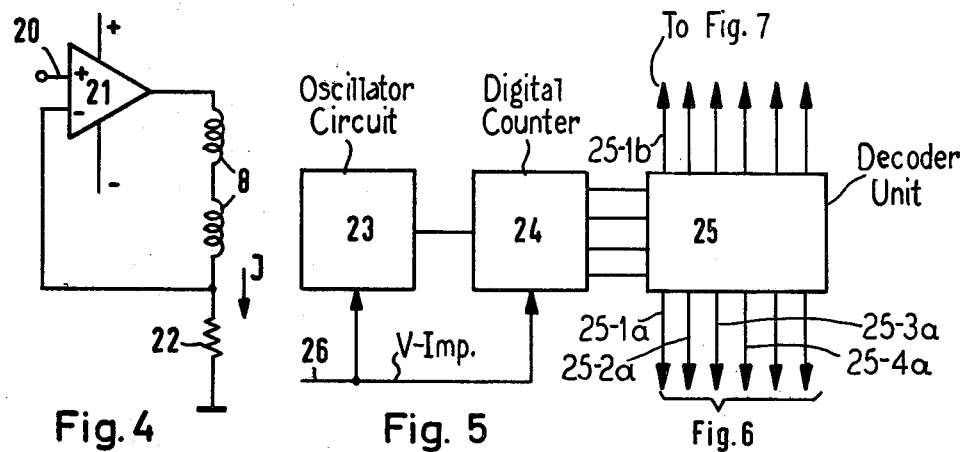
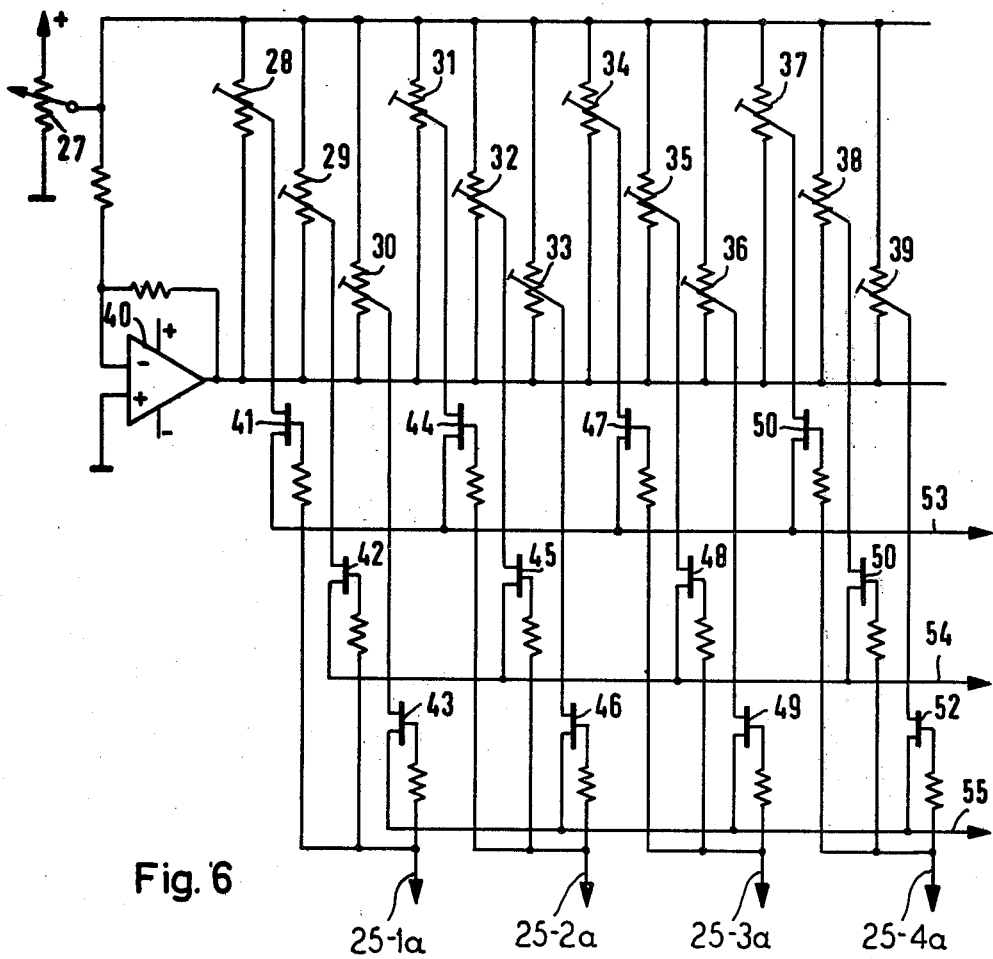
Fig. 4    Fig. 5
Fig. 6

X-RAY DIAGNOSTIC INSTALLATION FOR X-RAY TOMOGRAPHIC IMAGES

BACKGROUND OF THE INVENTION

The invention relates to an X-ray diagnostic installation for producing X-ray tomographic images comprising a support table, means for producing an X-ray beam penetrating a patient lying on the support table, on the one side, and an image detection installation on the other side of the support table, and a device for moving the X-ray beam and the image field of the image detection installation in mutually opposite directions so that sharply defined images are formed of only those details disposed in a specified longitudinal layer of the body which has been determined by the swivelling axis of the X-ray beam.

X-ray diagnostic installations of this type are known wherein, in order to produce the X-ray beam, an X-ray tube is mounted at the one end of a guide rod, which bears a cassette carrier for X-ray film cassettes at its other end and which is capable of pivoting about the swivel axis for the purpose of changing the direction of the X-ray beam. In order to produce tomograms on an X-ray film disposed in a cassette, the X-ray tube and the cassette carrier are moved in opposite directions relative to one another such that sharply defined images are produced on the X-ray film of only details of that particular body layer traversed by the swivel axis. Image-formation of all remaining details is more or less strongly blurred.

The disadvantage in the case of the known X-ray diagnostic installations comprising a mechanical, opposite movement of the X-ray tube and cassette carrier is that the time required for the preparation of a tomographic image is comparatively long due to the necessary mechanical movement, so that motional blurrings can occur, and that a comparatively great constructional outlay is necessitated on account of the required mechanical movement. In addition, only images of longitudinal layers of the body can be produced in the manner described.

SUMMARY OF THE INVENTION

The object which is the basis of the invention consists in producing an X-ray diagnostic installation of the type cited initially with which tomographic images can be produced without necessitating for this purpose a mechanical movement of an X-ray tube or of a film carrier.

In accordance with the invention, this object is achieved by virtue of the fact that a number of X-ray tubes is provided for the purpose of producing and moving the X-ray beam, one of said X-ray tubes being capable of being switched on, respectively, in step-by-step fashion by means of a control generator, that the image detection installation consists of an X-ray image intensifier associated with a deflection device, synchronized by the control generator, for the output image of the image intensifier, and that means are provided for the reproduction of the output image of the X-ray image intensifier. These means can be provided by an individual image (or single-shot) camera and/or a cinematographic camera and/or a TV camera with an output-connected video unit. These cameras may be coupled to the output of the X-ray image intensifier by way of a switchable; i.e., partially transmissive, mirror system.

In the case of the inventive X-ray diagnostic installation, the X-ray beam is, on the one hand, advanced by means of a step-by-step switching-on of the X-ray tubes; i.e., without mechanical tube-movement. In addition, while the X-ray image intensifier remains in a stationary condition, an image deflection takes place e.g. via deflection coils. Accordingly, a very rapid tomographic image representation is possible; for example, within the half-image time (or field) of the television system. This tomographic image representation time; i.e., the time required for a complete tomographic operating cycle, may also be selected to be shorter for an indirect X-ray image intensifier photograph or a cinematography image. The selection of the layer plane proceeds by changing the field strength of the magnetic deflection of the output image of the image intensifier. In addition to the production of a tomogram by means of photographing the image on the video unit or the output image of the X-ray image intensifier, it is also possible to carry out tomographic fluoroscopies.

In fluoroscopic tomographic examination, it is possible, through the use of an image intensifier camera, to produce directed tomograms; namely, short-time tomograms in the millisecond range. Directed tomograms were not hitherto possible. In addition, heart-phase controlled tomograms are realizable.

The randomly variable tomographic (or laminographic) height adjustment through the intensity change of the magnetic image intensifier output image deflection permits length-measurements. The measurement of areas (or surfaces) or volumes is thereby also realizable. The readout procedure can take place directly on a calibrated potentiometer scale, for example, on a sliding potentiometer, or on an electronic measuring instrument, for example, a digital voltmeter. However, the deflection amplitudes can also be converted to a coded form for subsequent data processing.

The tomographic (or laminographic) height adjustment can be changed in a step-by-step fashion in the case of each television field or television frame. The frame or image frequency of the television system can amount to 50 to 60 Hz, or it can also be increased during rapid through-flow of contrast media. Subsequent to a preselectable number of layers, the magnetic deflection of the output image of the image amplifier can be reset to the deflection for the first layer, such that traversal of layers begins anew. During a filling of a contrast medium and also during removal of a contrast medium in the case of an organ such as e.g. the kidney, tomographic images of the entire organ are obtained through this procedure for each filling phase. Pursuant to fluoroscopic control, the tomographic (or laminographic) height can also be determined prior to contrast medium injection, possibly with a short test injection. The individual television images which represent a specified layer each time can be recorded via the X-ray television chain on a video tape storage, or they can be recorded by an image intensifier-cine camera channel, and they can be analyzed image-by-image subsequent to examination.

With two X-ray tube systems, it is possible to alternately produce right and left stereoscopic images in succession, and to photograph said images via a cine camera or an X-ray television chain with an image frequency of e.g. 100 Hz.

A particularly expedient further development of the invention consists in that an analog or digital storage is provided for the video signal which storage facility is actuated by the control generator in such a fashion that the data of predetermined image lines or image points of consecutive images are stored in the latter, and that there is connected to said storage a video display unit for the simultaneous reproduction of the line-or image-point data stored in the storage, said reproduction proceeding in a linear successive fashion. In this further development, it is possible to store the data of discrete longitudinal body layers by changing the body longitudinal layer in the same image line of consecutive images, and, in this manner, to reproduce a cross-sectional image of the body on the video unit connected to the storage. If the data of the same image line of consecutive X-ray images, which correspond to different longitudinal body layers, are not stored in the storage, but if, on the contrary, the data of successive image lines of consecutive television images are stored therein, it is possible to reproduce on the video unit connected to the storage the image of a layer running obliquely through the body.

This shall be explained further in the following on the basis of a sample embodiment and other objects, features and advantages of the invention will be apparent from the following detailed description taken in connection with the accompanying sheets of drawings.

BRIEF DESCRIPTION OF THE DRAWINGS

FIGS. 4 through 10 illustrate exemplary circuit details for the components of the installation according to FIG. 1.

DETAILED DESCRIPTION

Figure 1:
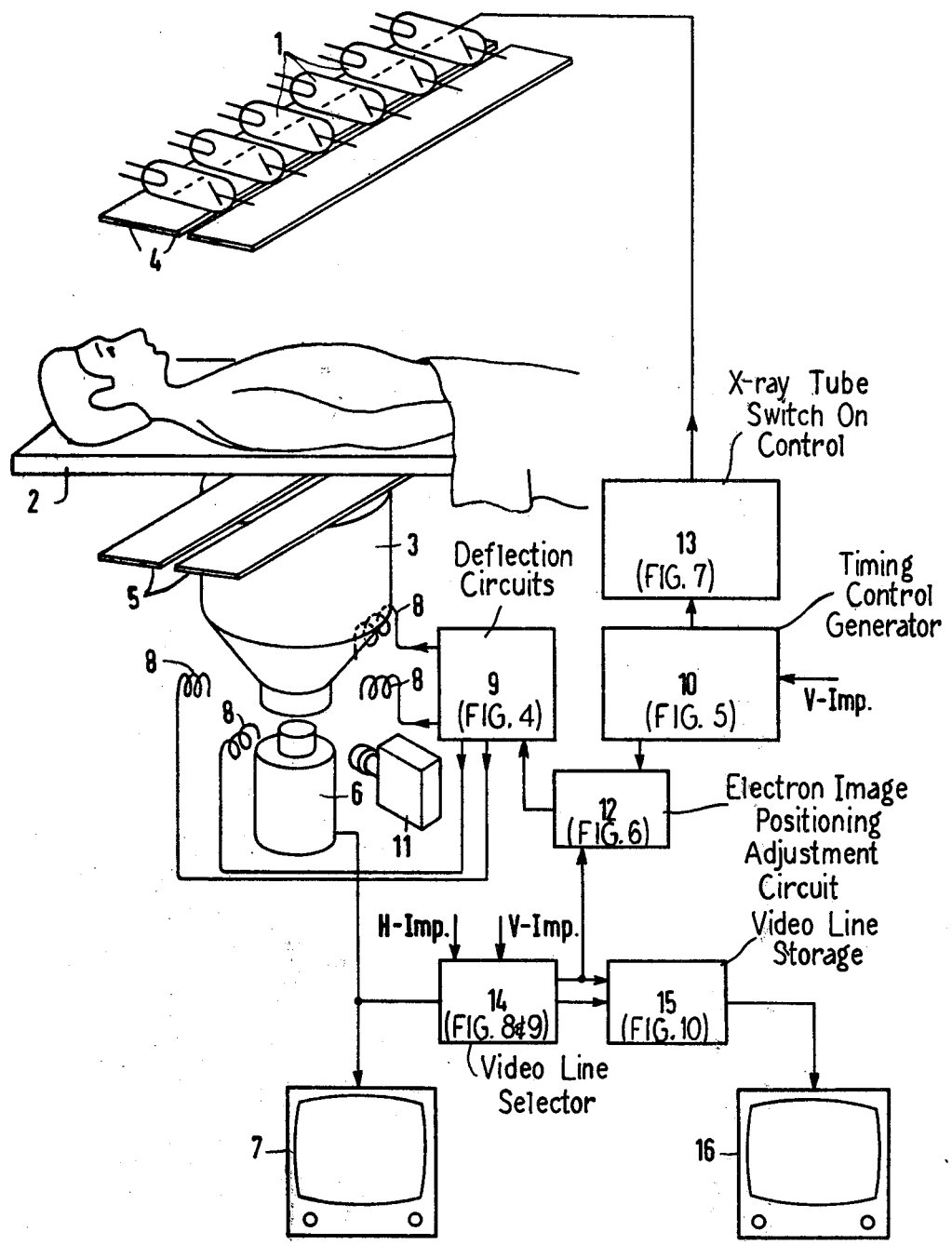
FIG. 1 is a diagrammatic illustration of an X-ray diagnosis installation in accordance with the invention.

The installation illustrated in FIG. 1 manifests six X-ray tubes 1, arranged in a row, which are provided with control grids. The high voltage generator for the X-ray tubes 1 is not illustrated. X-ray tubes 1 transilluminate a patient lying on a support table 2, and produce X-ray images on the inlet screen of an X-ray image intensifier 3. In order to reduce the stray radiation and the radiation load on the patient, slit diaphragms 4 and 5 are arranged between the X-ray tubes 1 and the patient, and between the support table 2 and the inlet screen of image intensifier 3 respectively, for the purpose of preparing transverse tomographic images. The output image of image intensifier 3 is picked up by a television camera 6 and reproduced on a video unit 7. The electron-image of X-ray intensifier 3 is magnetically deflected by means of two pairs of deflecting coils 8. Actuation of deflection coils 8 proceeds by means of a deflection component 9 which is synchronized by a control generator 10. Position displacement is effected through a displacement device 12. Control generator 10 brings about, in synchronism with the image displacement in image intensifier 3, the step-by-step switching-on of the X-ray tubes 1 via a control device 13 to which the grids of X-ray tubes are individually connected.

There is connected to the output of television camera 6 a video line selector 14 which, like timing control generator 10, is synchronized by the field synchronizing impulses (V-Imp., FIG. 1) of the picture blanking and synchronizing signal for the television system. Line selector 14 effects the input of the data of predetermined image lines into a video line storage 15. Output of the data in storage 15 can proceed, synchronized by control generator 10, to a video unit 16 on which, in contrast with video unit 7, cross sectional images of the body are represented.

Let it first be assumed that diaphragms 4 and 5 are not present. In this case, the reproduction of a longitudinal tomographic image of the body on video unit 7 is possible. Control generator 10 ensures that the X-ray beam issuing from the X-ray tube arrangement 1 is moved by a step-by-step switching-on of one of the X-ray tubes 1 at a time and that the output image of the X-ray image intensifier is moved via the displacement device (or positioning adjustment circuit) 12 and the deflection circuits 9 in a direction opposite thereto, so that sharply defined images are formed on video unit 7 of only those details lying in a specified longitudinal section or longitudinally disposed layer as determined by the swivelling axis of the X-ray beam, whereas the details lying outside this specified longitudinal layer of the body are reproduced in a blurred fashion.

Figure 2:
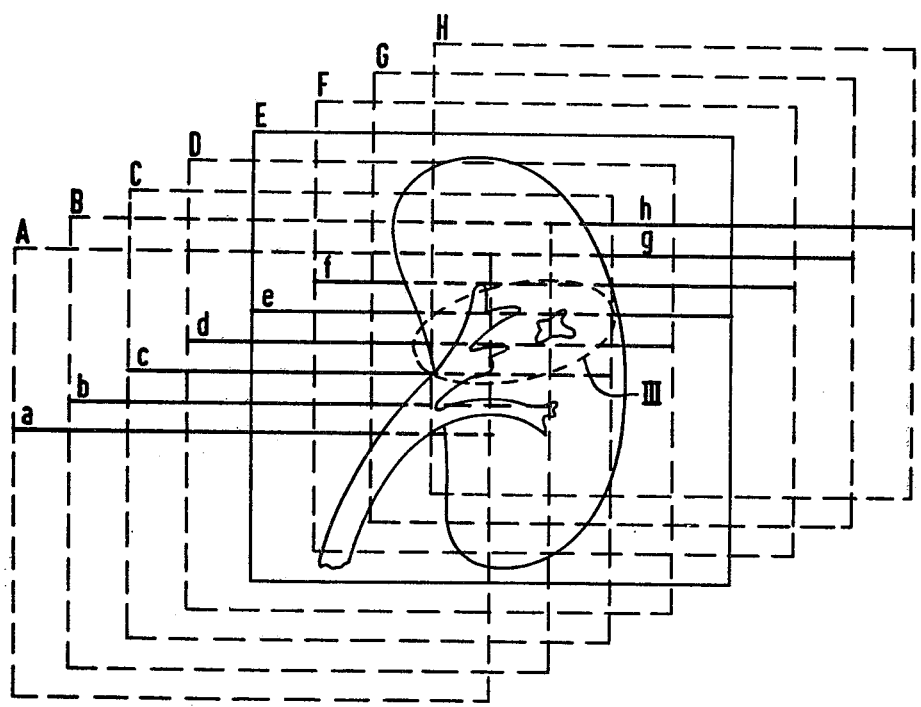
FIG. 2 is a diagram showing a longitudinal tomographic image prepared with the installation according to FIG. 1.

In addition to being selected by means of intensity change in the magnetic deflection for the image intensifier output image, the depth of the longitudinal layer of the body whose details are to be sharply (or clearly) represented on the video unit 7 can also be selected by means of adjustment of the distance between X-ray tubes 1 and the patient support table 2 as well as image intensifier 3. In accordance with FIG. 2, corresponding to the selected body layer, one out of a plurality of A through H longitudinal tomographic image regions can be represented on video unit 7. FIG. 2 illustrates by way of example a longitudinal tomographic image E of the human kidney. (The image region E is represented by the solid line rectangle in FIG. 2 having the letter E at the upper left corner.)

By means of line selector 14, it is possible to store in storage 15 the data of predetermined image lines of consecutive longitudinal tomographic images. This shall be explained further in the following on the basis of FIGS. 2 and 3.

FIG. 2 illustrates as an example that the data of image lines designated by letters a through h which lie in the consecutive longitudinal tomographic image regions A through H, respectively, are input into storage 15. The image lines a through h of the individual longitudinal tomographic image regions have a common position in the respective image regions A through H, (as is graphically indicated in FIG. 2 by the similar location of each line a through h in the respective rectangles with the respective letters A through H in the upper left corners thereof). If storage 15 is subsequently interrogated by its conventional readout system in such a manner that the data of image lines a through h are all reproduced on video unit 16 in linear consecutive fashion, an image such as that shown in FIG. 3 results; i.e., a cross-sectional image III' corresponding to the plane indicated by dash line III in FIG. 2. (FIG. 3 shows by the positions of lines a through h, the successive depths of the planar image regions A through H in relation to cross-sectional image plane III in FIG. 2.)

Figure 3:
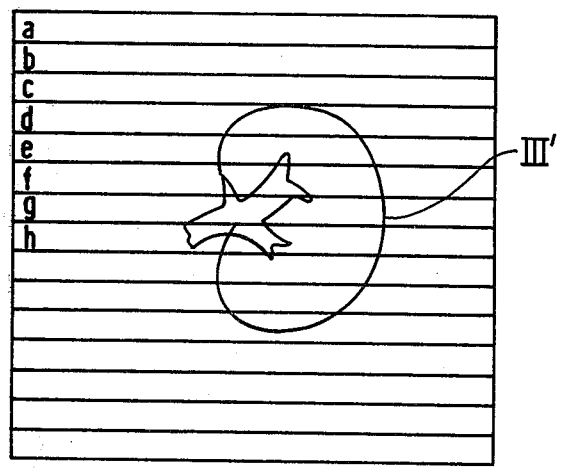
FIG. 3 illustrates a transverse tomographic image prepared with the installation according to FIG. 1.

In the image recording example in accordance with FIGS. 2 and 3, the same image line of consecutive longitudinal tomographic image regions is input in storage 15. It is also possible to input to storage 15 the data of consecutive image lines of consecutive longitudinal tomographic images, e.g. for longitudinal tomographic image region A, the data of the 100th image line; for longitudinal tomographic image region B, the data of the 101st image line; for longitudinal tomographic image region C, the data of the 102nd image line, etc. In this manner, an oblique tomographic image representation is possible through interrogation of storage 15, and through linear consecutive reproduction of its data.

If only the reproduction of body cross-sectional images on the video unit 16 is desirable, diaphragms 4 and 5 in accordance with FIG. 1 can be provided, so that only a thin strip-like section of each of the particular image regions (such as A through H) is scanned in which the image lines (such as a through h, FIG. 2) of interest are disposed.

Within the framework of the invention, it is not necessary for the X-ray tubes 1 according to FIG. 1 to be in a linear arrangement. For example, a circular or other random X-ray tube arrangement is also conceivable with a corresponding magnetic deflection of the electron image in image intensifier 3.

A complete image recording operating sequence; i.e., the recording of an entire longitudinal tomographic image, can take place during the time period of a television half-image (field). In the case of a 50 Hz image frequency television system, this time amounts to 20 ms; in the case of a 100 Hz image frequency television system, it amounts to 10 ms. For image intensifier photographs, it is also possible to select shorter times for the photographic sequence. The shortest limit time is dependent upon the maximum permissible X-ray tube power.

Instead of storing the data of predetermined image lines or the entire image data of longitudinal tomographic images in storage 15, it is also possible to store a selected portion of the data of each image line. Thus, it is also possible to select and store only partial regions of the longitudinal tomographic images.

Within the framework of the invention, it is also possible to photograph the X-ray image intensifier output images in the form of tomographic images by means of an individual image camera (or single-shot camera) or by means of a cine camera 11.

FIG. 4 illustrates the construction of the deflection device 9. The voltage from the displacement device 12 reaches a deflection amplifier 21 via the input 20. The voltage drop at resistance 22, brought about by deflection current J, is transmitted to the inverting input of this highly amplifying deflection amplifier 21. There results a negative current feedback; i.e., the deflection current is proportional to the applied input voltage at 20.

In accordance with FIG. 5, control generator 10 manifests a digital oscillator 23 which delivers pulses which are counted by a digital counter 24 and are conveyed in the binary code to a decoder unit 25. The output signals of this decoder 25 are utilized in order to control the displacement device 12 and the control device 13. Counter 24 and oscillator 23 are reset via line 26 e.g. by means of the vertical (or field synchronizing-)impulses V-Imp., FIG. 1, of the television chain of the television system.

FIG. 6 illustrates the construction of the displacement device 12. The tomographic (or laminographic) height is adjusted with a resistance 27. The adjusted voltage is conveyed to the one end of all adjusting resistances 28 through 39 for the purpose of position adjustment. In addition, the voltage is inverted by an inverter 40; i.e., it is connected, with equal amplitude and opposite polarity, to the other end of all adjusting resistances. With the adjusting resistances 28 through 39, the respective magnetic deflection of the electron image produced by each X-ray tube at the X-ray image intensifier output is adjusted such that all the images of one layer become superimposed. Three adjusting resistances are associated with each X-ray tube. The signals for controlling switching transistors 41 through 52 are supplied by the control generator according to FIG. 5; namely, its decoder 25. Lines 53, 54, 55 lead to deflection device 9; namely, to an input such as 20, FIG. 4, of one deflection amplifier such as 21 in each instance, three sets of jointly acting deflection coils 8 being actually provided in accordance with the embodiment of FIG. 6, the sets being offset by 120° from each other (one set being omitted in FIG. 1 for clarity of illustration).

Figure 7:
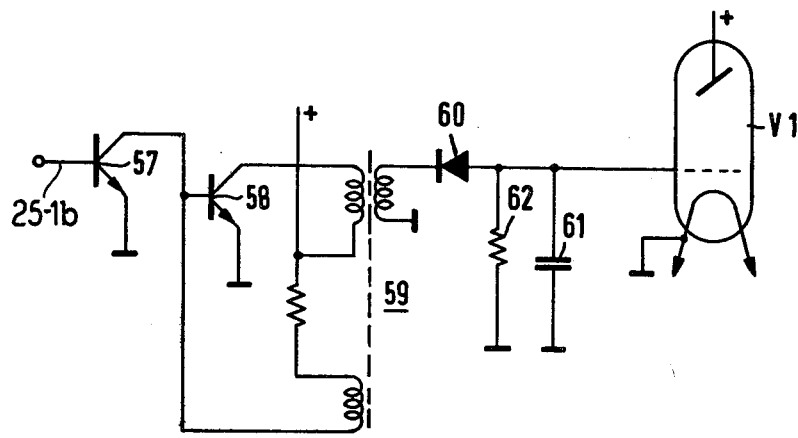

FIG. 7 illustrates the construction of control device 13. The control signal of control generator 10 starts and blocks an oscillator with a transistor 58 via a transistor 57. The transformer 59 of the oscillator delivers a voltage via a diode 60 when said oscillator is switched on, which voltage smoothed by a capacitor 61, blocks the associated X-ray tube (such as V1). Upon switching off of the oscillator, capacitor 61 is discharged via a resistance 62, and the X-ray tube draws current.

Figure 8:
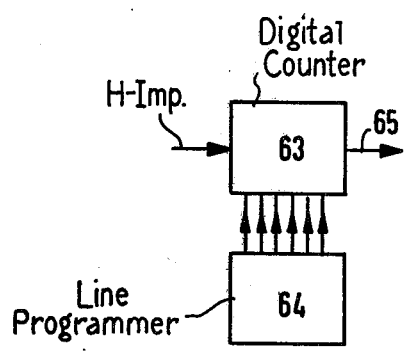

The components of line selector 14 illustrated in FIG. 8 include a digital counter 63 for the horizontal (or line) synchronization pulses (H-Imp., FIG. 1) which permits the selection of any random line of a television image. For a cross-sectional image, the adjustment of the line remains fixed; for an oblique sectional image, the programming of the line selector must be changed during an operating cycle through the discrete layer depths (such as indicated at A through H in FIG. 2). A line programmer 64 is connected to counter 63 so that a pulse will appear at output 65 with the programmed line.

Figure 9:
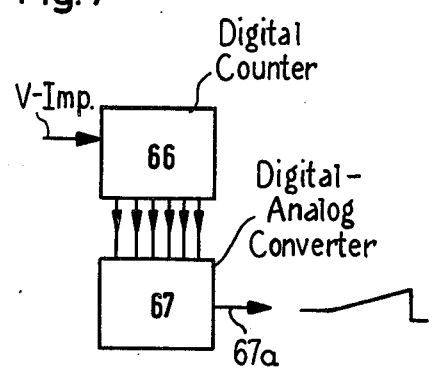

Simultaneously, by means of a vertical (or field-synchronizing) pulse counter 66, FIG. 9, with a following digital-analog converter 67, a slow sawtooth is produced at line selector 14, which sawtooth shifts the layer depth in the case of each television half image (or field) via the displacement device 12, thereby replacing the manual adjustment of the layer depth (which is effected by resistance 27, FIG. 6, of the displacement device 12 as previously described).

Figure 10:
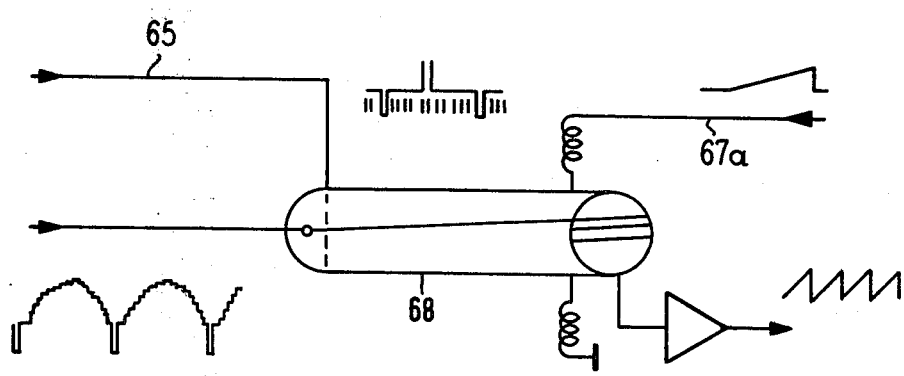

Storage 15, in accordance with FIG. 10, can be e.g. a storage tube 68 to the cathode of which the television signal of video unit 7 is conveyed. The output pulse of the line selector 14 ensures, by gating of the storage tube, that only one storage of the selected line takes place. During the operating sequence of the discrete tomographic images, the vertical deflection of the storage tube is operated with the slow sawtooth produced in the line selector 14, so that the same line of the television signal of television camera 6, with the different information of the discrete layers, is in each instance written on an adjacent line of the target of storage tube 68.

After the writing-in operation and the switching-off of the X-radiation, the vertical deflection is switched over to the conventional frequency and the charge which has been inscribed in linear fashion is read out in a half-image field cycle in the form of a cross-sectional image.

SUMMARY OF THE OPERATION

Production of a Longitudinal Layer Image (FIG. 2)

In operation of the exemplary embodiment for the production of a laminographic layer image of a desired depth, (such as at the depth represented by image region E shown in solid lines in FIG. 2), the diaphragm plates 4 and 5 are omitted, and the tubes 1 are arranged to produce sequential beams of suitable cross section (e.g. conical) which are each limited so as to extend through the longitudinal layer region to be recorded and onto the receiving inlet of image intensifier 3. The transmitted radiation images will then impinge on successive offset but overlapping areas on the inlet face of the image intensifier.

The electron image positioning adjustment circuit 12, FIG. 1, is set up so that the image field of the image intensifier is shifted in step with the shifting of the beam and in the opposite direction. Specifically for the exemplary circuit of FIG. 6, the resistances 28–39 are adjusted such that the transmitted images with respect to the selected longitudinal layer region (such as that represented by the rectangle designated with the letter E in FIG. 2) become superimposed at the output of the image intensifier.

For the case where a longitudinal layer such as indicated at E, FIG. 2, is to be scanned, the potentiometer 27, FIG. 6, may be adjusted to select the range of magnetic deflection of the image intensifier 3 so as to correspond to the selected layer. This range is then fixed during the layer scanning operation, so that the output at 67a, FIG. 9, is not supplied to the circuit of FIG. 6 in this case. Components 14, 15 and 16, FIG. 1, are not required where only a single longitudinal layer is to be scanned during a given operating cycle.

The tubes 1 may have operating voltages applied to the filaments and between cathode and anode thereof, but with each grid circuit receiving a blocking potential by means of an individual tube control circuit of component 13 such as that specifically shown in FIG. 7.

The timing control generator 10 may comprise a decoder circuit 25 which with counter 24 in its reset condition maintains each of the base circuits of transistors such as 57 in FIG. 7 in a cut-off condition. (Transistor 58, FIG. 7, is then operative to provide the blocking potential at the associated X-ray tube.) Then for a fluoroscopic examination, oscillator 23 may be enabled to supply pulses to binary counter 24. At a first selected binary count value of counter 24, decoder 25 may supply a turn-on pulse to respective first output lines thereof (such as 25-1a and 25-1b), one turn-on pulse being operative to switch on transistor 57, FIG. 7, and thus to turn off transistor 58. The first tube V1 of the series of tubes 1, FIG. 1, is thus unblocked for the time interval required to recharge capacitor 61 to the blocking potential. When the counter 24 reaches a second selected count value, the second output lines of decoder 25 supply a turn-on pulse which momentarily activates the second tube of the tubes 1 of FIG. 1. The tubes are in this way cyclically unblocked in sequence to repeatedly scan the selected layer during a fluoroscopic operation.

For the sake of a diagrammatic showing, decoder unit 25 is shown as having six outputs at the lower side thereof which are coupled to respective lines such as indicated at 25-1a, 25-2a, 25-3a, 25-4a, in FIG. 6. Similar outputs are indicated at the upper side thereof which are coupled to the respective tube control circuits such as that shown in FIG. 7. For the sake of diagrammatic correlation, reference numerals 25-1a through 25-4a and 25-1b have been applied to the outputs of decoder 25 in FIG. 5 to indicate the operative association of these outputs with the correspondingly designated inputs in FIGS. 6 and 7.

Longitudinal Measurement During Tomographic Fluoroscopy

Since for a given size image at the output of the image intensifier, the setting of the depth adjustment potentiometer 27, FIG. 6, will be a function of the actual length measurement of the image, length measurements can be obtained by calibrating the potentiometer 27. The readout can take place directly by means of a calibrated potentiometer scale; for example, a calibrated scale on a sliding potentiometer. Alternatively, a digital voltmeter may be coupled to the movable contact of potentiometer 27 to register the magnitude of the magnetic deflection amplitude. However deflection amplitudes can also be converted to a coded form by means of an analog to digital converter connected with the moving contact of potentiometer 27.

Production of Transverse Layer Images (FIG. 3)

In operation of the exemplary embodiment to produce cross sectional tomographic images, the diaphragm plates 4 and 5 are positioned so that the beams produced by tubes 1 are restricted to a thin body cross section of interest. The line selector 14, in this instance, is connected with the image adjustment circuit 12, (as is actually shown in FIG. 1 by the line leading from the upper output of selector 14 to component 12 in FIG. 1). Referring to FIG. 9 the sawtooth waveform supplied by converter 67 is suitably coupled to the circuit of FIG. 6 at the location of potentiometer 27, so that the image fields controlled by the circuit of FIGS. 5 and 6, sequentially scan the transmitted radiation images corresponding to layer regions of different depth (such as those represented by rectangles marked A through H in FIG. 2). For example, with the diaphragm plates 4 and 5 aligning the beams with the cross section indicated at III in FIG. 2, the sources 1 will scan lines a through h lying in the plane of section III, so as to record a cross sectional image region as diagrammatically indicated in FIG. 3 including image III' of the body organ of interest.

For this type of operation, line selector 14 is set to select the line of each field of camera 6 which corresponds to the plane III, FIG. 2, being scanned. For the specific line selector circuit of FIG. 8, the programmer 64 would be set to the desired line number, and counter 63 would count in step with the line deflection of camera 6 during each active field scanning cycle.

As soon as the camera 6 completed a field scan cycle, the line selector 14, FIG. 1, would shift the deflection magnetic fields of image intensifier 3 to a new amplitude value corresponding to a new image depth and storage 15 would be corresponding offset to a new line storage position. Thus referring to the example of FIG. 9, the vertical pulse following a field scan by camera 6 would step counter 66 to its next counter condition, and correspondingly shift the analog output from converter 67. The new analog signal from converter 67 would shift the image focus to the next image depth (via a circuit such as shown in FIG. 6) and would shift the vertical deflection current of the analog storage tube 68 of FIG.

10, for example. The desired cross-sectional image (such as indicated in FIG. 3) would then be stored as a charge image by tube 68, FIG. 10, for display via video unit 16, FIG. 1.

Where operation of the illustrative embodiment is to produce a transverse sectional image of a layer disposed obliquely, the gaps between diaphragm plates 4 and 5 can be of a size (or orientation) corresponding to such obliquely disposed layer, so that each successive linear segment in the layer is sequentially scanned by the beams from tubes 1. In this case programmer 64, FIG. 8, must be set to a new line number after each gating pulse to the grid of the storage tube of FIG. 10. The depth deflection control circuit of FIG. 9 again causes tomographic scanning at successive desired depths, by means of the circuit shown in FIG. 6, and successive vertical offsetting of the line storage tube 68, FIG. 10. Each successive gating pulse at 65, FIGS. 8 and 10, will then select a different number line from camera 8 for each successive tomographic layer which is scanned. The reference numeral 65 has been applied in FIG. 10, and the reference numeral 67a has been applied in FIGS. 9 and 10, for the sake of a diagrammatic indication of the operative relationship between the respective outputs and inputs.

In FIG. 1, parenthetical figure designations have been applied to the various components, to indicate for the sake of convenience the figures giving illustrative details for implementing these components, such parenthetical references being given by way of example only, and not for the purpose of limitation of such components in FIG. 1.

It will be apparent that many modifications and variations may be effected without departing from the scope of the novel concepts and teachings of the present invention.

We claim as our invention:

1. A diagnostic installation for producing tomographic images, comprising a support, radiation source means at one side of the support for producing a beam penetrating a patient on the support, an image detection installation on the opposite side of the support having an image field for detecting the transmitted beam, and scanning means for shifting the beam and the image field of the image detection installation in mutually opposite directions such that sharply defined images are produced only for those details lying in a selected longitudinal layer of the body, said source means comprising a number of individually actuatable sources capable of being activated one at a time, said scanning means comprising a control generator controlling said sources for activation of the sources one at a time in step-by-step fashion for shifting said beam, said image detection installation comprising an image intensifier having a deflectable image, and said scanning means further comprising image deflection means operable for shifting the image field of the image intensifier oppositely to the shifting of the beam, and image processing means for processing the output image of the image intensifier for tomographic image reproduction.

2. An installation according to claim 1, characterized in that said image processing means comprises a television chain (6, 7) including a television camera (6) at the image intensifier output and a video unit (7) for the immediate reproduction of the tomographic images.

3. An installation according to claim 2, characterized in that said image processing means further comprises storage means (15) for the video signal from the television camera for storing data of predetermined portions of successive television images, and a video unit (16) connected to the storage means (15) for the purpose of display of the data stored in said storage means (15).

4. An installation according to claim 3, characterized in that the storage means (15) is controlled such that the data of the same image lines of consecutive television images are stored therein.

5. An installation according to claim 3, characterized in that the storage means (15) is controlled such that the data of different portions of consecutive television images are stored in the latter.

6. An installation according to claim 1, characterized in that the scanning means comprises a displacement device (12), synchronized by the control generator (10), and including potentiometer means (27) for the adjustment of the shifting of the image field and hence the adjustment of the tomographic height, which potentiometer means (27), renders possible a longitudinal measurement during tomographic fluoroscopy.

7. An installation according to claim 1, characterized in that the scanning means comprises a displacement device (12), synchronized by the control generator (10), and providing for the adjustment of tomographic height, and an electronic measuring apparatus for sensing the tomographic height is connected to the displacement device (12).

8. An installation according to claim 7, characterized in that the electronic measuring apparatus comprises an analog to digital converter for coding the intensity of the magnetic deflection for the image intensifier output image.

9. An installation according to claim 1, characterized in that the scanning means provides for the step-by-step control of the intensity of the magnetic deflection for the output image of the X-ray image intensifier in dependence upon an image frequency.

10. An installation according to claim 1, characterized in that two like X-ray tube systems are provided for a spatial reproduction of the tomographic images by means of alternate recording of a right and a left tomographic image.

* * * * *